United States Patent
Wong et al.

(10) Patent No.: US 6,557,102 B1
(45) Date of Patent: Apr. 29, 2003

(54) DIGITAL TRUST CENTER FOR MEDICAL IMAGE AUTHENTICATION

(75) Inventors: Stephen T. Wong, San Francisco, CA (US); James Yuan-Pin Yu, Sunnyvale, CA (US)

(73) Assignee: Koninklijke Philips Electronics N.V., Eindhoven (NL)

(*) Notice: Subject to any disclaimer, the term of this patent is extended or adjusted under 35 U.S.C. 154(b) by 781 days.

(21) Appl. No.: 08/924,867

(22) Filed: Sep. 5, 1997

(51) Int. Cl.[7] .............................. H04L 9/00; G06F 17/60
(52) U.S. Cl. ............................ 713/176; 713/176; 705/3
(58) Field of Search ................... 380/5, 4, 23; 713/155, 713/161, 178

(56) References Cited

U.S. PATENT DOCUMENTS

| | | | | | |
|---|---|---|---|---|---|
| 4,833,625 A | * | 5/1989 | Fisher et al. | ................. | 364/518 |
| 5,050,212 A | * | 9/1991 | Dyson | .......................... | 380/25 |
| 5,136,647 A | * | 8/1992 | Haber et al. | ................... | 380/49 |
| 5,367,672 A | | 11/1994 | Takagi | ......................... | 395/600 |
| 5,546,572 A | | 8/1996 | Seto et al. | ................... | 395/600 |
| 5,579,393 A | * | 11/1996 | Conner et al. | ................ | 380/25 |
| 5,706,457 A | | 1/1998 | Dwyer et al. | ................. | 395/349 |

FOREIGN PATENT DOCUMENTS

EP     0332322 A2    2/1989    ........... G06F/15/40

OTHER PUBLICATIONS

Schneier, Bruce. Applied Cryptography: Protocols, Algorithms, and Source Code in C. Chapter 10 p. 226, 1996*

"A Crypotologic Based Trust Center for Medical Images", S. Wong, Journal of the American Medical Informatics Association, vol. 3, No. 6, Nov./Dec. 1996, p. 410–421.

* cited by examiner

*Primary Examiner*—Gail Hayes
*Assistant Examiner*—Jenise Jackson
(74) *Attorney, Agent, or Firm*—John Vodopia (57) ABSTRACT

A medical image management system including an image archive server for storing image datasets received from a plurality of image acquisition computers and a plurality of display stations for displaying requested image datasets retrieved from the image archive server is provided with an authentication and security system which includes an authentication server for maintaining and storing hashes and timestamps, and for providing hash, timestamp pairs in encrypted form in response to requests from display stations. The image acquisition computers are configured for computing hashes and providing them and image dataset identifiers to the authentication server, receiving timestamps from the authentication server which are then inserted in the image datasets, and storing the image datasets in the image archive server. The display stations are configured for retrieving image dataset, computing hashes from retrieved image datasets, requesting and decrypting hash/timestamp pairs received from the authentication server, and comparing the hashes, and optionally the timestamps, obtained from the authentication server with those computed or extracted from the image datasets received from the image archive server.

18 Claims, 7 Drawing Sheets

DIGITAL TRUST CENTER FOR MEDICAL IMAGE AUTHENTICATION

BACKGROUND OF THE INVENTION

1. Field of the Invention

The present invention relates generally to systems for management of image information including digital images and associated data by maintaining at least one central electronic archive which may be accessed over a digital data network or other communications link by remote viewing stations. In its particular aspects, the present invention relates to Picture Archiving and Communications Systems (PACS) or similar systems for medical images in association with a so-called "digital trust center" for enabling authentication of the image information.

2. Description of the Related Art

Such a system is described in S. Wong, "A Cryptologic Based Trust Center for Medical Images", Journal of the American Medical Informatics Association, Vol. 3 No. 6, Nov./Dec. 1996, pp. 410–421, written by one of the inventors herein.

Image management systems for hospitals and similar healthcare giving organizations, which systems are known by the acronym PACS, may serve an entire hospital department, such as radiology, an entire hospital, or multiple hospitals. For the purposes of this application, PACS refers to a system devoted to the management of digital medical images or the pertinent part of a data management system for hospital or patient information which includes these functions. In a PACS, digital images acquired from image acquisition devices such as X-ray, CT, MRI, PET, nuclear medicine, and ultrasound, or the scanning of film, and data associated with such images are sent electronically by their respective associated acquisition computers over a local or wide area network to a central PACS archive server, which accesses and manages an electronic image data store or archive. Identified images may then be requested electronically at any of plurality of remote viewing or display stations in communication with the PACS archive server via the network or another communications link, such as a telephone line, in response to which request, they are retrieved by the PACS archive server from the data store and sent to the requesting station.

Particularly as such systems become more ubiquitous and extensive in size, and network links or gateways are provided to other information system resources of the institution, and possibly to the Internet, the potential exists for unauthorized access to the workstations, networks or servers of the system by persons of malevolent intent. Consequently, in addition to the possibility of files being corrupted by equipment malfunction, there is the danger of acts of sabotage where images could be surreptitiously substituted or modified in the data store or injected into the network. The use of spurious or corrupted images for purposes of diagnosis or treatment could, of course, have disastrous consequences for the patient. Further, there is the danger that unauthorized persons could obtain the medical images and/or other private electronic medical records with the intent of using them for improper purposes.

The cited article indicates that it would be beneficial to integrate cryptographic techniques and PACS to protect the confidentiality and determine the authenticity of digital images in hospitals using a so-called "digital trust center" in which an authentication server is provided to attach a hash value (a so called "digital fingerprint") derived from the image data set to an incoming image dataset so that the hash is stored with the image data set in the image data store maintained by the PACS archive server. In response to a query from a display station identifying the image by ID number or patient name, the PACS archive server can check the authenticity of the image data set by comparing the stored hash with one it computes from the stored image data set.

The system suggested by the cited article is unacceptably vulnerable to attack or compromise of authenticity and security in the link(s) between the acquisition computers closely associated with the various imaging devices and the PACS archive server and in the link(s) between the archive server and the various display stations.

SUMMARY OF THE INVENTION

It is an object of the present invention to provide, in or in association with an image archive server or other information management system including management of images, an authentication and security system which includes at least partial image file encryption and extraction of authentication information at the image acquisition computers closely associated with the various imaging devices and which includes image file decryption and authentication at the display stations. It is another object of the present invention that authenticity be determined by comparing information derived from the image dataset at the time of authentication with independently maintained information previously captured by the image acquisition computers and maintained by an authentication server. Lastly, it is another object that the means or functionality for authentication and for security be integrated coherently into the centralized data management configuration of a PACS or similar system in a transparent and seamless manner, and that the demands of decryption and authentication be accomplished at the display stations with acceptable delays.

Briefly, the aforementioned and other objects are satisfied by providing in association with an image management system, an authentication and security system comprising an authentication server or so-called "digital trust center" which maintains and stores hashes and corresponding time stamps indicating the times of receipt of the respective hashes, and provides them on request in encrypted form, and further functionality in the image acquisition computers and the display stations to provide for security and to interact with the authentication server for authentication purposes. Thus the acquisition computers are configured for pre-processing image datasets of acquired digital images (or sequences of images) each image or sequence comprising a header and image data, including performing any required image compression, encrypting at least a portion of the image data, computing hashes and providing them to the authentication server, receiving time stamps from the authentication server, inserting the time stamps in the image headers, and sending the thereby modified image datasets to the image archive server. Further, the image display stations are configured for performing any required image decompression, decrypting image datasets, computing hashes from decrypted image datasets, obtaining and decrypting stored hashes from the authentication server and comparing the decrypted hashes obtained from the authentication server with the locally computed hashes. For more thorough authentication, the time stamps obtained from the authentication server, after decryption at the image display stations, may be compared with the time stamps contained in the image headers.

One further feature of the present invention is that in order to reduce the time to decrypt image datasets, only a portion of the image data is encrypted by the acquisition computers. Further, optionally, the image headers are encrypted at the image acquisition computers, and decrypted at the image display devices.

Other objects, features and advantages of the present invention will become apparent upon perusal of the following detailed description when taken in conjunction with the appended drawing, wherein:

DETAILED DESCRIPTION OF THE PREFERRED EMBODIMENTS

Figure 1:
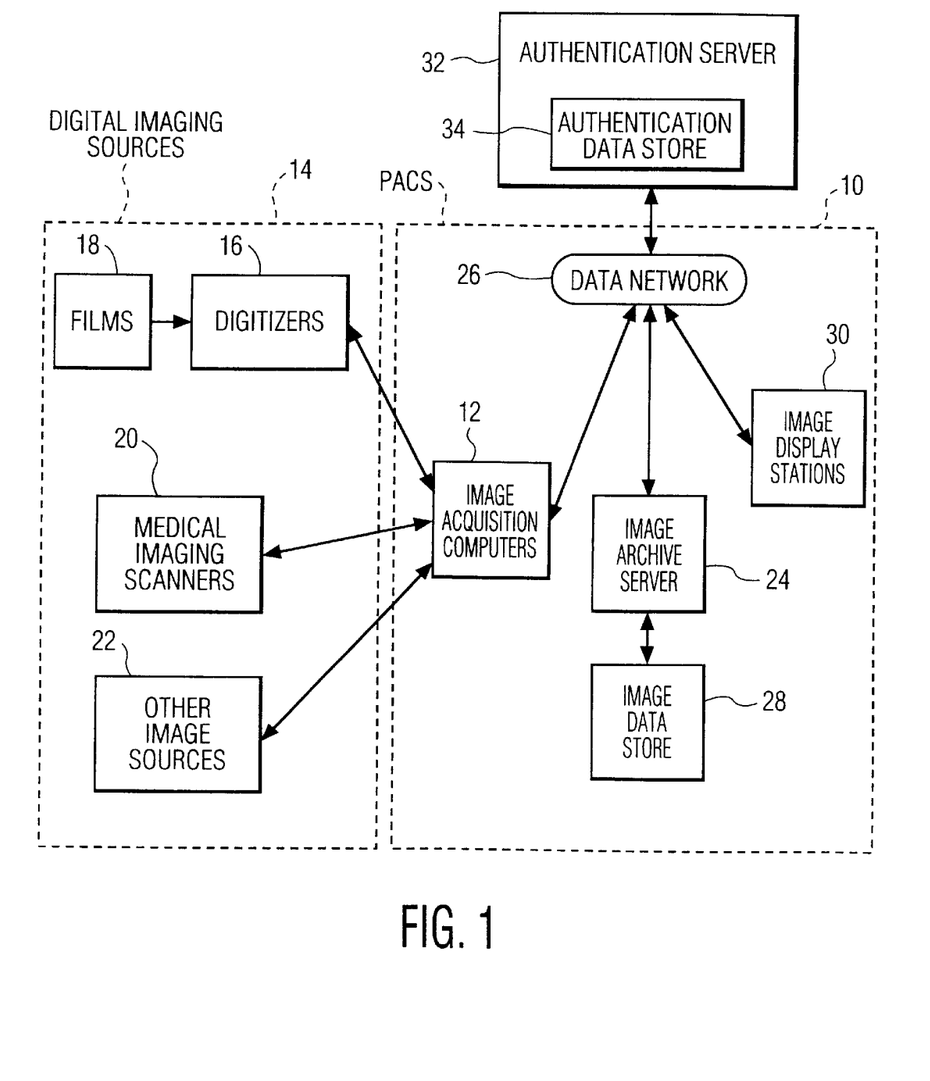
FIG. 1 is a schematic drawing of a system in accordance with the invention including acquisition computers, image display stations, an image archive server and an authentication server.

Referring first to FIG. 1 of the drawing, there is shown a picture archiving and communications system (PACS) or similar system 10 for management of digital medical images and associated data such as information identifying the patient, the study type, and the parameters employed in the imaging. Image management system 10 includes image acquisition computers 12 which receive or generate digital medical images in conjunction with digital imaging sources 14, which include digitizers 16 for scanning film 18 such as produced by conventional X-ray machines, medical imaging scanners 20 such as CT, MRI, PET, nuclear medicine, and ultrasound which provide digitized physical measurements to their respective acquisition computers to enable these computers to compute or generate images or a series of images, and other digital image sources, such as X-ray equipment including an X-ray image intensifier and camera chain (not shown) which directly produce images in electronic form. It should be understood that the acquisition computers 12 are, in general, separate computers which are each in close association with one or more of the respective digital imaging sources 14, and are typically proximate to the location(s) where the imaging (or scanning of film) by their associated digital imaging sources is performed. As is usual in the prior art, the acquisition computers are configured for reformatting the images to place them in a recognized standard format such as DICOM 3.0 (Digital Imaging Communication in Medicine) from the American College of Radiology/National Electrical Manufacturer's Association (ACR/NEMA).

In the usual PACS, the reformatted acquired image datasets are sent by the acquisition computers 12 to an image archive server 24 of the PACS via a data network 26 (e.g. ethernet) which datasets are stored in at least one image data store 28 maintained by image archive server 24. Further, as is conventional, numerous image display stations 30 are provided generally at locations remote from the digital imaging sources 14 served by data network 26 for retrieving via image archive server 24 image datasets stored in image data store 28, and for displaying the retrieved images. In the prior system, the image datasets are stored in the image data store 28 and subsequently retrieved therefrom for display without any steps having been taken in respect of assuring confidentiality or enabling authentication of the image datasets. The system in accordance with the present invention differs in that an authentication server 32 is provided in communication with the acquisition computers 12 and image display stations 30 via data network 26 and these devices are configured for cooperation to assure confidentiality and enable authentication using data in an authentication store 34 in or maintained by the authentication server.

Figure 2:
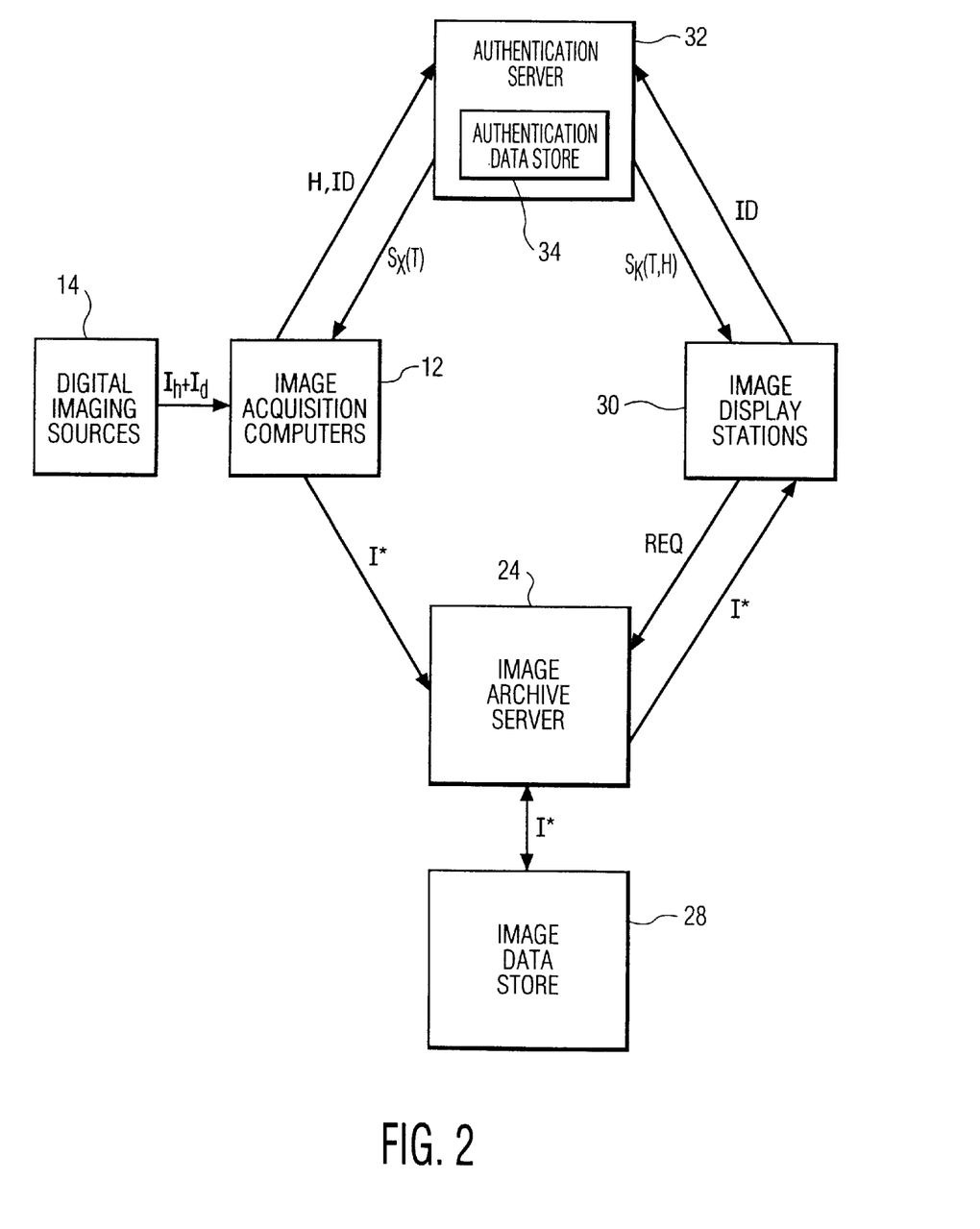
FIG. 2 depicts the data flow between the elements of FIG. 1.

The data flow illustrated in FIG. 2 between the devices of the system provide an overview of the nature of the interaction between devices of the system, particularly with respect to enabling authentication. As appears from FIG. 2, the digital imaging sources 14 provide to or cooperate with image acquisition computers 12 to generate image datasets or files comprising image headers $I_h$ and image data $I_d$. The image acquisition computers 12 compute hashes H and form identifiers from the image datasets and send the corresponding hash/identifier pairs to authentication server 32. The latter records timestamps T indicating the times and dates of its receipt of the hash/identifier pairs, saves the hashes, timestamps and identifiers in authentication store 34, and sends the timestamps in encrypted form $S_x(T)$, where S is the secret key encryption function and x is the secret key, back to the sending image acquisition computers. The sending image acquisition computers decrypt the timestamps and process and modify the image datasets using the timestamps to produce the pre-processed datasets I$^+$ in a manner which will be later explained in detail. The pre-processed datasets I$^+$ are sent by the image acquisition computers 12 to the image archive server 24, which in turn causes these to be stored in image data store 28.

Subsequently, when there is a need to retrieve and display the stored image at one of the image display stations 30, a request REQ identifying the needed image, as by patient name, is sent from the image display station to image archive server 24. The latter retrieves the preprocessed image dataset I$^+$ from the image data store 28 and sends it to the requesting image display station. At the image display station identifying information is extracted from the image dataset and the identifier ID is formed therefrom and sent to authentication server 32, in response to which the authentication server retrieves the timestamp T and hash H corresponding to the identifier ID from its authentication data store, and supplies the timestamp/hash pair in encrypted form $S_K(T,H)$, where S is the secret key encryption function and K is the secret key, to the requesting image display station 30. This information is decrypted at the display station using the secret key to obtain the timestamp/hash pair supplied by the authentication server. Also the image display station extracts the timestamp and computes the hash directly from the image dataset supplied by the image archive server 24. The comparison of the hashes obtained from different sources, and also if desired, the timestamps, provides a strong authentication by assuring that these items which were captured when the image dataset was first generated at the image acquisition computer still characterize the just received image dataset.

Figure 3:
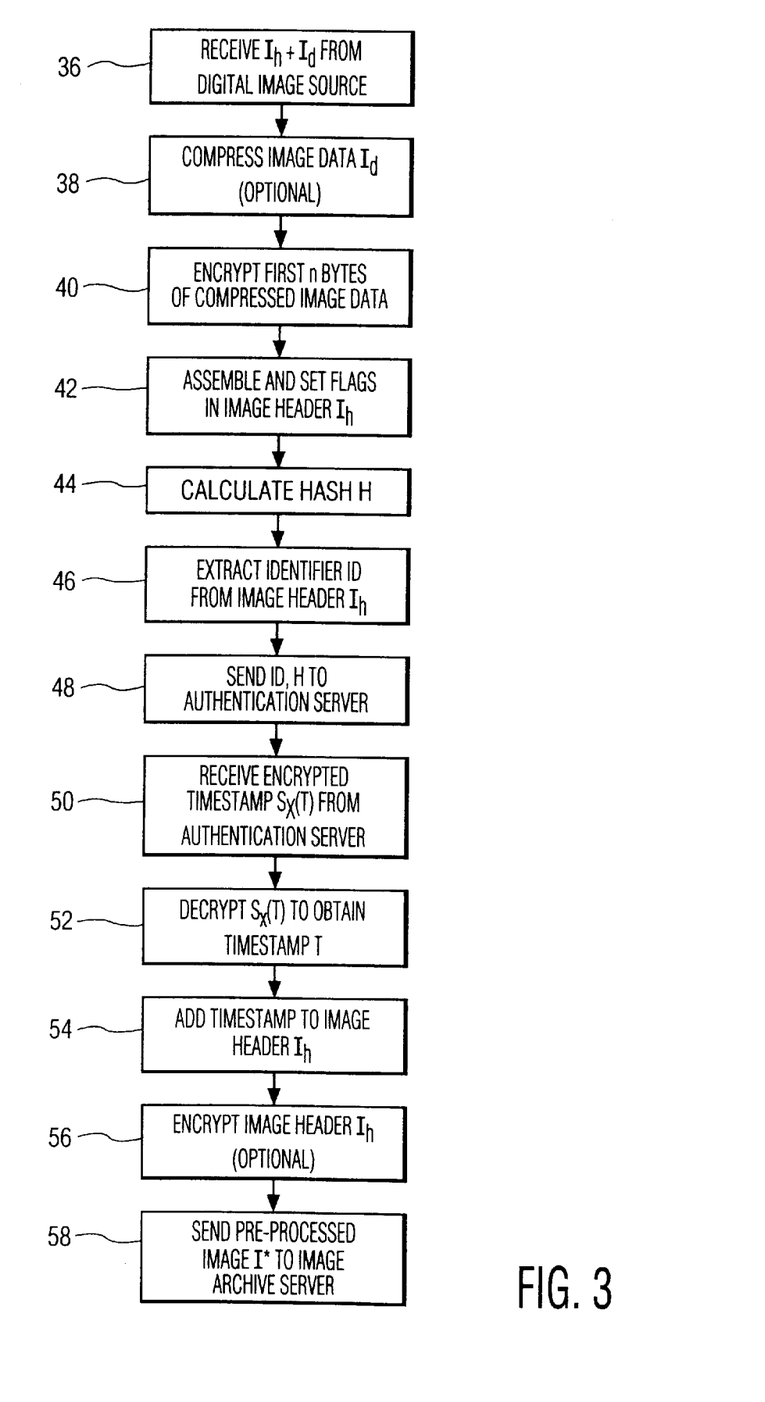
FIG. 3 is a flow chart indicating steps carried out in the acquisition computers of FIGS. 1 and 2.

Now, with the benefit of this overview, the steps performed in the image acquisition computers in respect of both assuring confidentiality as well as enabling authentication will now be explained with reference to FIG. 3. Therein, in step 36, the image dataset $I_d+I_h$ is received from the digital imaging source 14 and in step 38 the image data $I_d$ is compressed if desired, using a known compression algorithm, such as JPEG. For purposes of discussion, the compressed image data, or the raw image data if no compression was performed, is denoted L and its length $L_L$. Then in step 40, the first n bytes of this possibly compressed image data L is encrypted to form the data $N=E_K(n)$, having a length $L_N$, where E is a secret key encryption function and K is the secret key. The number n of first bits in image data L to be encrypted is chosen to be a minor fraction of the image data but yet sufficiently large to render the image unusable without decryption while being sufficiently short to allow the decryption to be performed at image display stations 30 in an acceptable delay on the order of a fraction of a second. Suitable values for n are in the range of tens to hundreds of bytes, a small fraction of an image study which is on the order megabytes. It should be appreciated that because the size of the encrypted data differs from the original data, it is very difficult for an intruder or hacker to determine the beginning point of unencrypted image data. The encryption function E can be an established encryption algorithm such as DES (Data Encryption Standard, 56 bit key) or IDEA (International Data Encryption Algorithm, 128 bit key) or chosen from numerous other encryption algorithms.

Figure 5:
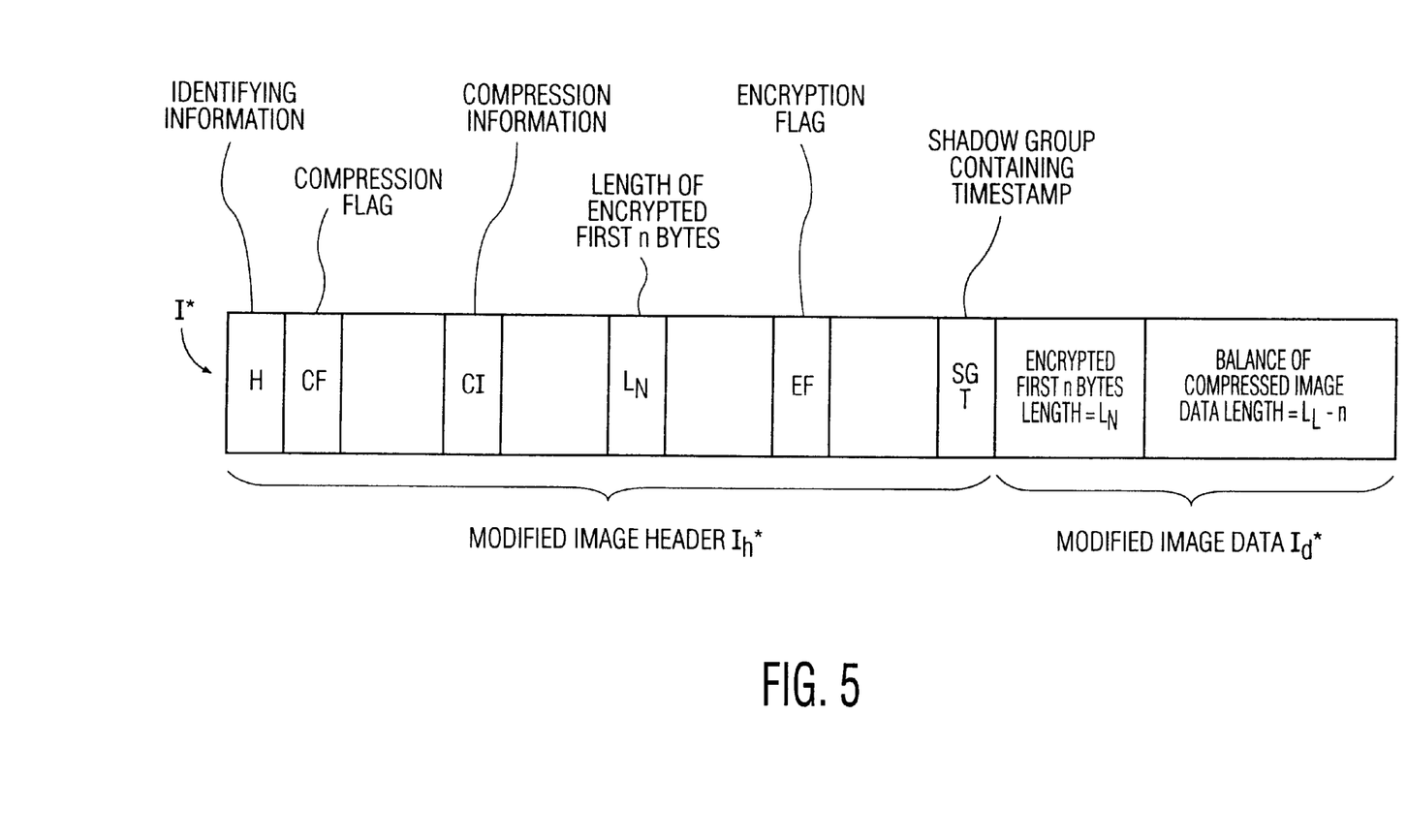
FIG. 5 shows the format of a pre-processed image file or dataset I$^+$ as a result of the steps in the flow charts in FIGS. 3 and 4.

In step 42, referring also to FIG. 5, modified image header $I_h^+$ and modified image data $I_d^+$ are formed and assembled into the pre-processed image dataset $I^+$ in a form suitable for archiving in PACS image data store 28, except for the timestamp T which has yet to be obtained authentication server 32. The modified image header $I_h^+$ comprises the usual identifying information II in image header $I_h$ obtained from or in conjunction with digital imaging sources and information which is set or inserted indicative of the pre-processing. The latter includes a compression flag CF which is set to indicate whether or not the image is compressed, inserted compression information CF identifying the type of compression, e.g. the algorithm employed, inserted length $L_N$ of the compressed first n bytes, and the encryption flag which is set to indicate that the image data has been encrypted. There is a shadow group SG in the modified image header $I_h^+$ into which the timestamp T will be later inserted. The modified image data $I_d^+$ is formed by concatenating the image data N of length $L_N$ and the balance of the image data L of length $L_L-n$.

Next, in steps 44, 46, and 48 a hash H is computed from the modified image data $I_d^+$, an identifier ID is formed from pertinent portions of the identifying information II extracted from the modified image header $I_H^+$, and the hash/identifier pair are sent to the authentication server. The hashing function used can be an established algorithm, such as MD4 (Message Group 4) or MD5 (Message Group 5), which produces a 128 bit hash value, or other hashing algorithm. The identifier should be unique and preferably comprise a combination of the hospital identification number, patient name, examination date, and study number.

The acquisition computer waits after sending the hash/identifier pair to the authentication server until in step 50 the encrypted timestamp $S_x(T)$ is received. In step 52 the received encrypted timestamp is decrypted using the secret key x to obtain timestamp T. Then, in step 54, the timestamp T is inserted in the modified image header $I_h^+$ portion of the modified image dataset $I^+$. Since no particular header field is provided in the DICOM 3.0 standard for a timestamp, timestamp T is inserted in the shadow group SG. Optionally, the modified modified image header $I_h^+$ may be encrypted in step 46 to provide an additional layer of security, since the header information is essential for identifying, decompressing, and decrypting the image dataset. After the optional substitution of an encrypted modified image header $I_h^+$ in the modified image dataset $I^+$, the latter is sent to image archive server 24 which causes the dataset to be stored in image data store 28.

Figure 4:
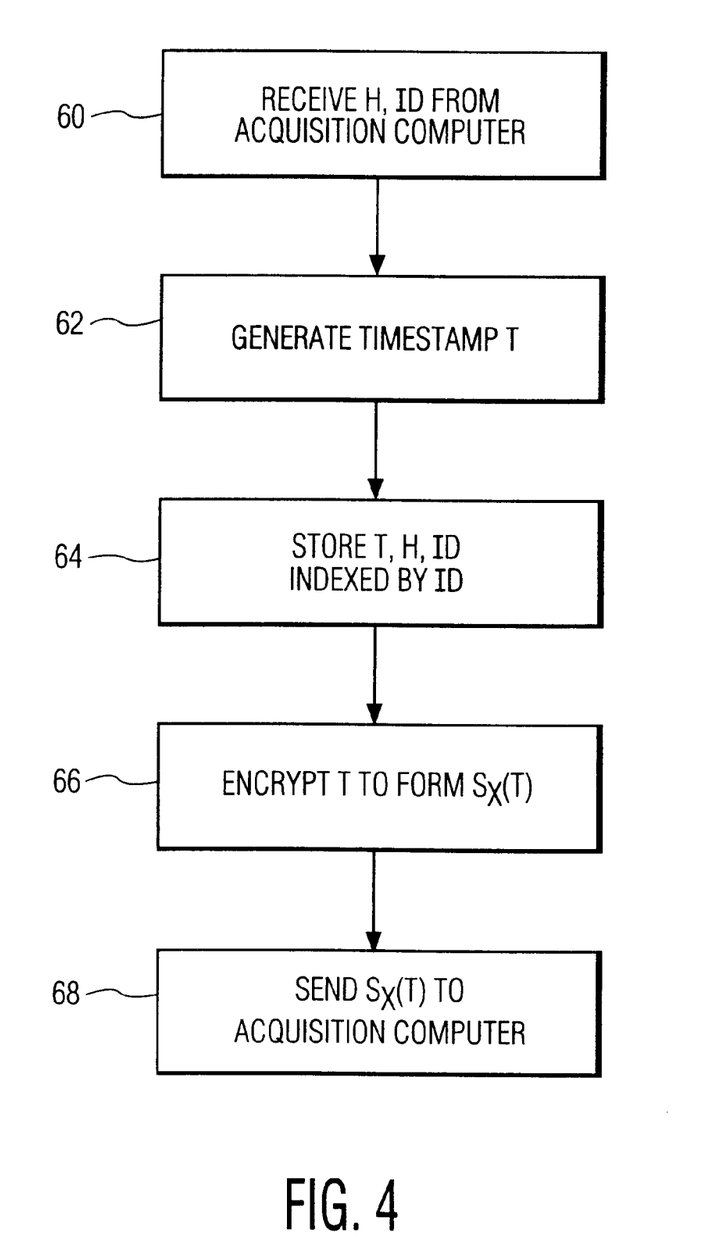
FIG. 4 is a flow chart of steps carried out in the authentication server in the course of interaction with one of the acquisition computers of FIGS. 1 and 2.

As shown in FIG. 4, the authentication server 32 in step 60 receives the hash/identifier pair from an acquisition computer 12 and in step 62, generates a timestamp T indicating the time of receipt. In step 64, the timestamp/hash/identifier trio are stored in the authentication data store 34 in the form of a database or similar data structure indexed or addressed by the identifier ID. The timestamp T is encrypted in step 66 to form $S_x(T)$, where S is the secret key encryption function, such as DES or IDEA, mentioned previously, and x the secret key, and in step 68, the encrypted timestamp is sent back to the acquisition computer 12 from which the hash/identifier pair was received.

Figure 6:
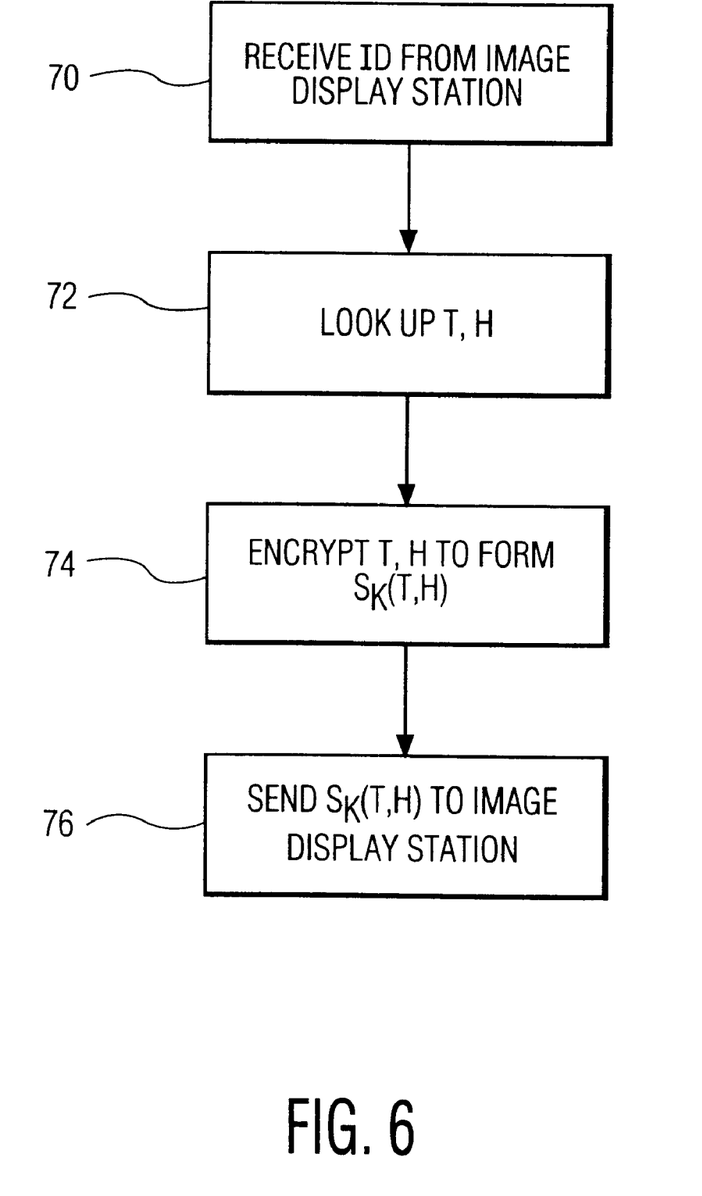
FIG. 6 is a flow chart of steps carried out in the authentication server in the course of interaction with one of the image display stations of FIGS. 1 and 2.

The steps carried out by the authentication server 32 in interacting with an image display station 30 are shown in FIG. 6. First an identifier ID is received from the display station in step 70. In response, using the identifier ID as an index, the corresponding timestamp T and hash H are looked up or retrieved from authentication data store 34. The timestamp/hash pair are encrypted to form $S_K(T,H)$, where H is the secret key encryption algorithm which is preferably the same as used by the authentication server in step 66 (FIG. 4) to encrypt the timestamp sent to the image acquisition computer 12, but with a different secret key K, and in step 76, the encrypted timestamp/hash pair is sent to the display station from which the identifier was received.

Figure 7:
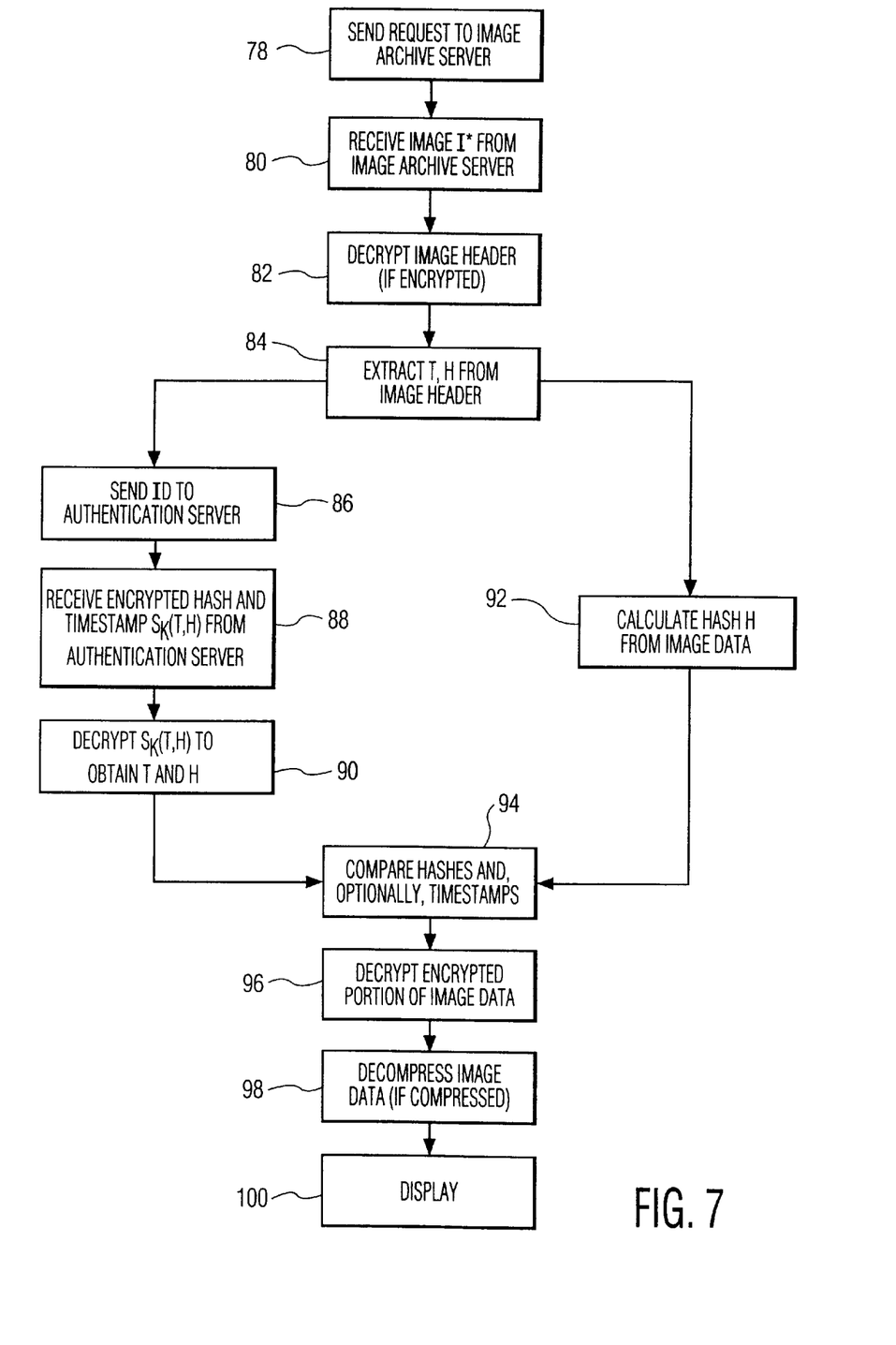
FIG. 7 is a flow chart of steps carried out in the image display computers of FIGS. 1 and 2.

The steps carried out by a display station 30 are shown in FIG. 7, which are initiated by in step 54 sending a REQ to the image archive server 24 for a particular image or study. The request may be negotiated by an interaction in which the user accesses a database or other search tool maintained by the image archive server, organized by patient names, dates and types of studies. In response to this request, the modified image dataset is retrieved by the image archive server 24 from image data store 28 and in step 80 received at the image display station. If the modified image header $I_h^+$ had been encrypted by the image acquisition computer 12 in step 56 (FIG. 3), then a decryption thereof is carried out in step 82 using the applicable decryption algorithm and secret key. Then, after any such decryption, the identifier ID and the timestamp T are extracted from the modified image header $I_h^+$.

In steps 86, 88 and 90, the identifier ID is sent to authentication server 32, an encrypted hash/timestamp $S_K(T, H)$ pair is received in response, and is decrypted using the appropriate decryption function and secret key K to obtain the timestamp T and hash H. Whereas, in step 92, the hash is computed by applying the same hashing function as applied by the acquisition computer in step 44 (FIG. 3) to the modified image data $I_{d+}$. In step 94, the hashes obtained in steps 90 and 92 are compared, and optionally for greater confidence of authenticity, also the time stamps obtained in steps 84 and 90 are also compared. If the compared items agree, authenticity is assumed and the image may be displayed and used for diagnostic purposes.

The image is obtained by, in step 96, decrypting the encrypted portion of length $L_N$ of the image data ($L_N$ being known from the header $I_h$) using the appropriate decryption function, which is preferably the same as used in step 88, but with a different secret key, to recover the first n bits of the image data. The recovered first n bits are concatenated with the balance of the image data to reconstruct the image data L of length $L_L$. Then in step 98, decompression is carried out, if compression had been carried out by the acquisition computer 12 in step 38 (FIG. 3) to recover the image data $I_d$. Whether compression was carried out and of what type is known from the compression flag and compression information fields CF, CI of the image header (FIG. 5). Lastly, in step 100, the image data $I_d$ is displayed as an image at the image display station 30.

While the use of secret key encryption has been described herein for enciphering even small textual messages such as time stamps T and hash values H passed between the authentication server 32 the PACS 10, it is pointed out that public key encryption, with its much stronger key management capabilities, could be used instead. This is because the much slower execution rate of public key encryption is tolerable for these small messages.

It should be apparent from the detailed description herein that the objects of the invention have been satisfied. However, while the present invention has been described in particular detail, it should also be appreciated that numerous modifications are possible within the intended spirit and scope of the invention.

For example, the present technique is readily applied to a system where an authentication server cooperates with a plurality of PACS, or with image management systems in a plurality of hospitals. Further, the present invention may be applied to other types of digital images, such as images of documents.

All references cited herein are incorporated herein by reference in their entirety and for all purposes to the same extent as if each individual publication or patent or patent application was specifically and individually indicated to be incorporated by reference in its entirety for all purposes.

What is claimed is:

1. In an image management system comprising image acquisition computers for acquiring image information from imaging devices associated with the image acquisition computers and forming image datasets, each comprising an image header and image data, an image archive server for receiving the image datasets from the acquisition computers and maintaining at least one image data store for the image datasets, and a plurality of remote display stations for displaying images from requested image datasets which are retrieved by the image archive server from the image data store and sent to the requesting display station, an authentication and security system comprising:

an authentication server for maintaining and storing pairs of hashes and identifiers, and for providing hashes in encrypted form in response to requests from display stations, wherein the requests include identifiers;

the acquisition computers being configured for pre-processing the image datasets, including performing any required image compression, encrypting at least a portion of the image datasets after any such compression, forming identifiers, computing hashes, providing pairs of hashes and identifiers to the authentication server, and sending pre-processed image datasets to the image archive server for storage in the image data store; and the display stations being configured for requesting and receiving identified pre-processed image datasets from the image archive server, decrypting the image datasets sent by the image archive server, performing any required data decompression on the image datasets, forming identifiers from the image datasets, computing hashes from the image datasets, sending requests including the formed identifiers to the authentication server, receiving identified hashes in encrypted form from the authentication server, decrypting hashes received from the authentication server, and comparing the hashes obtained from the authentication server with the hashes computed locally from the image datasets received from the image archive server.

2. The system of claim 1, wherein the authentication server is further configured for recording timestamps indicating the times of receipt of hashes and identifiers from the acquisition computers, for storing the hashes, identifiers and timestamps, for sending the timestamps back to the acquisition computers which sent the hashes and identifiers, and for sending the timestamps in encrypted form in response to requests from image display stations, and the acquisition computers are further configured for obtaining timestamps sent by the authentication server, and for including the obtained timestamps in the pre-processed image datasets which are sent to the image archive server.

3. The system of claim 2, wherein said authentication server is configured for sending the timestamps in encrypted form back to the acquisition computers which sent the hashes, and said acquisition computers are configured for decrypting the timestamps received from the authentication server.

4. The system of claim 2, wherein the image display stations are also configured for requesting identified timestamps from the authentication server, receiving and decrypting time stamps received from the authentication server, and comparing the decrypted timestamps received from the authentication server with the timestamps included in the image datasets received from the image archive server.

5. The system of claim 3, wherein the image display stations are also configured for requesting identified timestamps from the authentication server, receiving and decrypting time stamps received from the authentication server, and comparing the decrypted timestamps received from the authentication server with the timestamps included in the image datasets received from the image archive server.

6. The system of claim 1, wherein in the pre-processing performed by the acquisition computers only a minor fraction of the image data is encrypted.

7. The system of claim 2, wherein in the pre-processing performed by the acquisition computers only a minor fraction of the image data is encrypted.

8. The system of claim 3, wherein in the pre-processing performed by the acquisition computers only a minor fraction of the image data is encrypted.

9. The system of claim 4, wherein in the pre-processing performed by the acquisition computers only a minor fraction of the image data is encrypted.

10. The system of claim 5, wherein in the pre-processing performed by the acquisition computers only a minor fraction of the image data is encrypted.

11. The system of claim 1, wherein the pre-processing performed by the acquisition computers includes encrypting the image headers of the image datasets.

12. The system of claim 2, wherein the pre-processing performed by the acquisition computers includes encrypting the image headers of the image datasets.

13. The system of claim 3, wherein the pre-processing performed by the acquisition computers includes encrypting the image headers of the image datasets.

14. The system of claim 4, wherein the pre-processing performed by the acquisition computers includes encrypting the image headers of the image datasets.

15. The system of claim 5, wherein the pre-processing performed by the acquisition computers includes encrypting the image headers of the image datasets.

16. The system of claim 6, wherein the pre-processing performed by the acquisition computers includes encrypting the image headers of the image datasets.

17. The system of claim 7, wherein the pre-processing performed by the acquisition computers includes encrypting the image headers of the image datasets.

18. The system of claim 1 wherein the authentication server further comprises an authentication data store for storing the hashes and identifiers of the image datasets in the image data store.

\* \* \* \* \*